United States Patent [19]

Fritz et al.

[11] Patent Number: 4,707,549
[45] Date of Patent: Nov. 17, 1987

[54] PREPARATION OF ESTERS OF OPTICALLY ACTIVE 2-ARYLALKANOIC ACIDS

[75] Inventors: Gerhard Fritz, Dannstadt-Schauernheim; Manfred Eggersdorfer, Frankenthal; Hardo Siegel, Speyer, all of Fed. Rep. of Germany

[73] Assignee: BASF Aktiengesellschaft, Ludwigshafen, Fed. Rep. of Germany

[21] Appl. No.: 697,846

[22] Filed: Feb. 4, 1985

[30] Foreign Application Priority Data

Aug. 2, 1984 [DE] Fed. Rep. of Germany ....... 3404336

[51] Int. Cl.$^4$ .................... C07C 69/76; C07D 213/15; C07D 241/12; C07D 333/24
[52] U.S. Cl. ........................................ 544/336; 560/8; 560/100; 560/103; 546/174; 546/341; 549/79
[58] Field of Search ...................... 560/57, 8, 100, 103; 546/174, 341; 544/336; 549/79

[56] References Cited

U.S. PATENT DOCUMENTS 4,539,420 9/1985 Tsuchihashi et al. .......... 560/105 X

OTHER PUBLICATIONS

Nakajima et al., Bull. Chem. Soc. Jap. 52(8) (1979), pp. 2377–2382.
Derwent No. 18928K/08 (corresponds to Japanese Preliminary Published Application No. 8045/1983).
Masuda, et al., Chem. Abstracts, vol. 99 (1983), entry 121891n.
Masuda, et al., Chem. Abstracts, vol. 93 (1980), entry 46073z.
Segi, et al., Chem. Abstracts, vol. 96 (1982), entry 161783e.
Suga, et al., Chem. Abstracts, vol. 96 (1982), entry 51512h.

Primary Examiner—Mark L. Berch
Assistant Examiner—William A. Teoli, Jr.
Attorney, Agent, or Firm—John H. Shurtleff

[57] ABSTRACT

Esters of optically active 2-arylalkanoic acids I

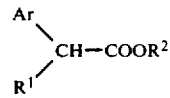

where Ar is an isocyclic or heterocyclic aryl radical and $R^1$ and $R^2$ are each $C_1$–$C_4$-alkyl, are prepared by subjecting an optically active ester II

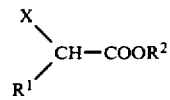

where X is Cl, Br or —O—SO$_2$—Y and Y is Cl or a hydrocarbon radical, to a Friedel-Crafts reaction with an aromatic compound ArH (III).

6 Claims, No Drawings

PREPARATION OF ESTERS OF OPTICALLY ACTIVE 2-ARYLALKANOIC ACIDS

The present invention relates to a novel process for the preparation of esters of optically active 2-arylalkanoic acids of the general formula I

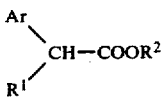

where Ar is an isocyclic or heterocyclic aryl radical and $R^1$ and $R^2$ are each $C_1$-$C_4$-alkyl.

It is well known that optically active compounds of this type have been prepared to date by converting the racemate of I to the racemate of the corresponding acid, reacting this racemate with an optically active amine to give a pair of diastereomeric salts, separating the last mentioned mixture into its two components by crystallization, obtaining the optically active acids from these components and then esterifying these acids again.

It is an object of the present invention to provide a simpler process for the preparation of the optically active compounds I, since the abovementioned classical method of resolving racemates is evidently inconvenient.

We have found that this object is achieved by a process for the preparation of the optically active 2-arylalkanoic acids I defined at the outset, wherein an optically active ester of the general formula II

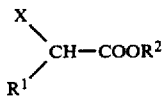

where X is chlorine, bromine or a radical Y—SO$_2$—O—, in which Y is chlorine or a hydrogen radical, is subjected to a Friedel-Crafts reaction with an aromatic compound ArH (III).

This process is particularly noteworthy, since it was known that the reaction of optically active compounds by the Friedel-Crafts method is acompanied by complete racemation of the enantiomers employed, a fact which is pointed out by, for example, Nakajima et al. in the introduction to their paper entitled "Alkylation of benzene with optically active 3-chloro-1-butanol . . ." (Bull. Chem. Soc. Jap. 52(8) (1979), page 2377 et seq.). Although an exception to this rule is reported here, this is explained in terms of the reaction taking place via a sixmembered ring formed as an intermediate from the chlorobutanol and AlCl$_3$. In the present case, however, the formation of such a 6-membered ring is not possible.

Those optically active starting compounds II which are unknown can be obtained in a simple manner, and with retention of the optical activity, from the corresponding esters of the optically active hydroxy acids IIa

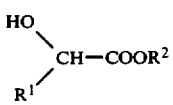

by reacting these, for example, with thionyl chloride or thionyl bromide, or with a sulfonyl chloride Y—SO$_2$—Cl in the presence of a base. Preferred radicals Y are chlorine, $C_1$-$C_4$-alkyl, in particular methyl, and benzyl, phenyl and 4-methylphenyl.

Particularly important starting compounds II are those which are derived from lactic acid (where $R^1$ is methyl), especially since their enantiomers are readily obtainable, for example by microbiological methods. Among the remaining compounds II, compounds which are also noteworthy are those in which $R^1$ is isopropyl. However, the novel reaction as such is virtually independent of the type of radical $R^1$, so that the latter depends on the properties of the products I as active compounds, or of the secondary products of these which are desired as end products.

The type of radical $R^2$ has no noticeable effect on the novel process; hence, for practical reasons, the simplest esters II are therefore generally used as starting materials, ie. the methyl or ethyl ester.

Examples of isocyclic and heterocyclic compounds III are the parent compounds benzene, naphthalene, anthracene, phenanthrene, pyridine, the pyrazines, quinoline and thiophene. These and other compounds III may carry substituents, eg. halogen, alkyl, alkoxy, aryl, carbalkoxy, acyloxy, cyano or nitro. For example, nonaromatic isocyalic or heterocyclic rings may also be fused to the parent aromatic compound.

Since the reaction of II with III generally takes place smoothly and completely, it is preferable to use these starting compounds in equimolar amounts. If III is a cheap substance, such as benzene or toluene, it may also be used in a molar excess over II, and also as a solvent.

Other suitable solvents are liquids which are inert under the reaction conditions, eg. carbon disulfide, nitroalkanes, nitrobenzene, acetonitrile, diethyl ether and dimethylformamide, as well as halohydrocarbons such as 1,2-dichloroethane, 1,1,2,2-tetrachloroethane, chloroform and carbon tetrachloride, provided relatively mild reaction conditions are employed.

Suitable Friedel-Crafts catalysts are the conventional Lewis acids which are used for this reaction, ie. primarily AlCl$_3$, ZnCl$_2$, FeCl$_3$ and BF$_3$. Since these compounds react in stoichiometric amounts, they are advantageously employed in an equimolar amount or a slight excess, based on II.

The reaction temperatures are from 0° to 100° C., preferably from 0° to 25° C., and the reaction is generally carried out under atmospheric or slightly superatomspheric pressure.

The reaction is otherwise carried out in a conventional manner, for example as described in Japanese Preliminary Published Application No. 8045/1983 for the reaction of racemic α-chlorosulfonyloxypropionates with benzene to racemic α-phenylpropionates.

The working up procedure for the reaction mixtures also has no special features, so that further description can be dispensed with.

The optically active products I are obtained in high yield and high optical purity. Some of these products are themselves important physiological active compounds, and some of them are intermediates for these and in general make a valuable contribution to the possible methods of synthesis in this field.

For example, S-(p-hydroxyphenyl)-α-isopropylacetates are important starting materials for synthetic pyrethroids, and d-(+)-6-methoxy-α-methyl-2-naphthaleneacetic acid is an anti-inflammatory agent and an antirheumatic agent.

EXAMPLE

Preparation of ethyl S-(+)- -phenylpropionate 43.3 g (0.2 mole) of ethyl S-(+)- -sulfonyloxypropionate were added to a solution of 94 g (1.2 moles) of benzene and 80 g (0.6 mole) of AlCl$_3$ in the course of one hour at 0°–10° C., and the mixture was stirred for a further 2 hours at 20° C. and then worked up in a conventional manner to give ethyl S-(+)-α-phenylpropionate. The yield was 76% and the optical purity 95%.

Ethyl α-sulfonyloxypropionate was prepared in virtually quantitative yield by reacting ethyl S-(−)-lactate with sulfuryl chloride at 0° C.

We claim:

1. A process for the preparation of an optically active 2-arylalkanoic acid ester of the formula

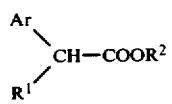   I where Ar is an aryl or heteroaromatic radical and R$^1$ and R$^2$ are each C$_1$-C$_4$-alkyl, which process comprises subjecting an optically active ester of the formula

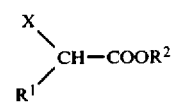   II where X is chlorine, bromine or a radical Y—SO$_2$—O—, in which Y is chlorine or a hydrocarbon radical, to a Friedel-Crafts reaction with an aromatic compound ArH (III) where Ar has the same meaning given above.

2. A process as claimed in claim 1, wherein X in the ester II is selected from the group consisting of chlorine, bromine and the radical Y—SO$_2$—O— in which Y is chlorine, C$_1$-C$_4$-alkyl, benzyl, phenyl and 4-methylphenyl.

3. A process as claimed in claim 1, wherein X in the ester II is the raical Y—SO$_2$—O— in which Y is methyl.

4. A process as claimed in claim 1, wherein R$_2$ in the ester II is methyl or ethyl.

5. A process as claimed in claim 1 carried out at a temperature of from 0° to 100° C. and under atmospheric or slightly superatmospheric pressure.

6. A process as claimed in claim 5 carried out at a temperature of 9° to 25° C.

* * * * *

UNITED STATES PATENT AND TRADEMARK OFFICE
CERTIFICATE OF CORRECTION

PATENT NO. : 4,707,549

DATED : November 17, 1987

INVENTOR(S) : Gerhard Fritz, Manfred Eggersdorfer and Hardo Siegel

It is certified that error appears in the above-identified patent and that said Letters Patent is hereby corrected as shown below:

Claim 6, last line: change the numeral "9" to -- 0 --.

Signed and Sealed this

Fourteenth Day of June, 1988

Attest:

DONALD J. QUIGG

Attesting Officer

Commissioner of Patents and Trademarks